United States Patent [19]

Cave

[11] Patent Number: 5,234,910
[45] Date of Patent: Aug. 10, 1993

[54] ACID INHIBITOR OF BACTERIAL ORIGIN

[75] Inventor: David R. Cave, Wayland, Mass.

[73] Assignee: University Hospital, Boston, Mass.

[21] Appl. No.: 595,044

[22] Filed: Oct. 10, 1990

Related U.S. Application Data

[63] Continuation-in-part of Ser. No. 381,781, Jul. 18, 1989, abandoned.

[51] Int. Cl.$^5$ .................. A61K 37/02; A61K 35/74; C12N 1/20; C07K 15/04
[52] U.S. Cl. .................. 514/21; 424/520; 530/825; 514/2; 514/926; 435/822
[58] Field of Search .............. 424/93, 520; 514/2, 514/21, 926; 530/825; 435/71.2, 822, 909

[56] References Cited

U.S. PATENT DOCUMENTS 4,882,271  11/1989  Evans et al. ..................... 435/7

OTHER PUBLICATIONS

Carrick et al., Biol. Abstracts vol. 88:63276 (1989).
Hill et al, Biol. Abstracts, vol. 85:80064 (1987).
Cave, D. R. and M. Vargas, Supplement to Gastroenterology, 96:A79 (May 1989 Abstract).
Janik, D. S. and D. R. Cave, Gastroduodenal Disease and *Campylobacter Pylori*, University of Virginia Conference (May 10-12, 1989), Abstract.
Cave, D. R. and M. Vargas, *The Lancet*, Jul. 22, 1989, pp. 187-189.
Barthel, J. S. et al., *Arch. Intern. Med.*, 148:1149-1151 (1988).
Morris, A. and G. Nicholson, *Am J. Gastroenterol.*, 82:192-199 (1987).
Blaser, M. T., *Gastroenterology*, 93:371-383 (1987).
Newell, D. G. et al., *J. Med. Microbiol.*, 27:41-44 (1988).
Lee, A. et al., *Infect. Immun.*, 56:2843-2850 (1988).
Hazell, S. L. and A. Lee, *The Lancet*, Jul. 5, 1986, pp. 15-17.
Henry, G. A. et al., *Am. J. Vet. Res.*, 48:831-836 (1987).
Kawano, S. et al., *Gastroenterology*, 96:A252 (1989).
King, William and Cave, David R., Abstract P-38 In: Enfermedades Digestivas, Gastroduodenal Pathology and *Helicobacter Pylori*, Third Workshop of the European *Helicobacter pylori* Study Group (Supplement I):25 (Nov. 1990).

Primary Examiner—Jacqueline Stone
Attorney, Agent, or Firm—Hamilton, Brook, Smith & Reynolds

[57] ABSTRACT

An acid inhibitor of bacterial origin which is effective in inhibiting acid secretion from gastric parietal cells; a method of producing this acid inhibitor; a method of administering the acid inhibitor to reduce acid secretion by parietal cells; and a therapeutic composition, which includes the acid inhibitor, for use in the method. In particular, the invention relates to a protein produced by gastric *Spirilla*, such as *Helicobacter pylori* (*H. pylori*), which is effective in inhibiting acid secretion by parietal cells and, thus, can be used in the treatment of peptic ulcer disease and other conditions of the gastroduodenal tract in which there is a tendency for ulceration.

3 Claims, 5 Drawing Sheets

FIG. 5

ACID INHIBITOR OF BACTERIAL ORIGIN

RELATED APPLICATION

This application is a continuation-in-part application of U.S. Ser. No. 07/381,781, entitled "Acid Inhibitor of Bacterial Origin" by David R. Cave, filed Jul. 18, 1989 and now abandoned. The teachings of the cited application are incorporated herein by reference.

BACKGROUND

Typically, the human stomach secretes approximately 2 liters of hydrochloric acid daily which is a strong acid secreted by the gastric parietal cells. Hydrochloric acid plays an important role in digestion, both directly (i.e., by reducing large food particles in size) and indirectly (i.e., by activating some of the gastric enzymes, such as pepsin).

Normally, the walls of the stomach and small intestine are protected from the potentially damaging effects of this strong acid. For example, the mucosal surface of the stomach is lined with cells which secrete a slightly alkaline mucus, which covers the stomach surface and serves to neutralize hydrogen ions, thus serving as a chemical barrier between the acid and the cells. Further, the cell membranes which line the stomach have limited permeability to hydrogen ions, which are prevented from entering into the underlying mucosa. Constant replacement of the mucus cells which line the stomach walls also helps protect the mucosa.

Despite these protective mechanisms, in many people, the gastric and duodenal mucosa becomes eroded or ulcerated and the damage may be very severe. The causes of such gastric or duodenal erosions or ulcers are unknown, but are regarded as a combination of an imbalance between progressive and protective factors. Many methods of treating ulcers and the accompanying pain, including administration of a variety of drugs to prevent or reduce acid secretion, to buffer the effects of secreted acid, and to coat the gastric mucosa with a protective film, have been tried. Although there are presently numerous drugs of value in such treatment, each has limitations. Particularly useful would be an agent or drug effective in reducing or preventing acid secretion by parietal cells because such an agent or drug would make it possible to minimize the quantity of acid present in the stomach and duodenum and, thus, avoid further irritation of or damage to either organ.

DISCLOSURE OF THE INVENTION

The present invention relates to an acid inhibitor of bacterial origin which is effective in inhibiting acid secretion from gastric parietal cells; a method of producing this acid inhibitor; a method of administering the acid inhibitor to reduce acid secretion by parietal cells; and a therapeutic composition which includes the acid inhibitor, for use in the method.

In particular, the present invention relates to a protein produced by gastric Spirilla, such as *Helicobacter pylori* (*H. pylori*), which is effective in inhibiting acid secretion by parietal cells and, thus, can be used in the treatment of peptic ulcer disease and other conditions of the gastroduodenal tract in which there is a tendency for ulceration. Until recently, *H. pylori* was known as *Campylobacter pylori* (*C. pylori*). The protein has been shown to be moderately heat stable, to be unable to pass through a dialysis membrane, and to be destroyed by pronase, but not by trypsin. The entire protein or an active portion of the protein can be administered orally or parenterally (e.g., intravenously) to reduce acid secretion in an individual.

The protein has been shown, using a standard assay technique, to be at least as effective in inhibiting parietal cell acid secretion as is cimetidine (a histamine analogue/antagonist often used to treat peptic ulcer and hypersecretory conditions).

DETAILED DESCRIPTION OF THE INVENTION

The present invention is based on the demonstration that *Helicobacter* species, such as *H. pylori, H. felis* and a Helicobacter-like isolate from Rhesus monkey, inhibit acid secretion from parietal cells of mammalian origin, as demonstrated using a standard assay method. *H. pylori*, as a whole organism or as a sonicate, has been shown to profoundly inhibit stimulated acid secretion from parietal cells of mammalian origin, as measured by the uptake and retention of [$^{14}$C]AP within parietal cells. Soll, A. H., *J. Physiol.*, 238:366-367 (1980). As described in detail in Example 1, *H. pylori* strains were isolated from the stomachs of three patients with chronic gastritis, duodenal ulcer and near normal mucosa. Histamine and IMX were used to stimulate rabbit parietal cells and uptake of [$^{14}$C]AP by the cells in the presence or absence of *H. pylori* (the whole organism or its sonicate) was determined. As described in Example 3, *H. felis* (from cat) and a Helicobacter-like organism isolated from Rhesus monkey have also been shown to profoundly inhibit acid secretion. The characteristic morphology of the organism *H. felis*, revealed by electron microscopy, makes identification of it and similar bacteria easy. Bacteria of this morphology have been identified in parietal cells of the mouse. Similar observations have been made in dogs (Henry, G. A. et al., *A. J. Vet. Res.*, 48:831–836 (1987)) and man (Chen, X. G. et al., *A. J. Clin. Path.*, (1986)). It is reasonable to expect that bacteria from parietal cells from mice, dogs and other animals have the same ability to inhibit acid secretion as that evidenced by other *Helicobacter* (e.g., *H. pylori, H. felis*). Preliminary results also indicate that *H. mustelae*, a Helicobacter species isolated from ferret demonstrate acid inhibiting activity. In contrast, other (non-Helicobacter) organisms had relatively little effect on acid secretion.

As a result, it has been shown that Helicobacter, as the whole organism or its sonicate, is very effective in inhibiting acid secretion (i.e., to a degree that is at least comparable with the effect of $10^{-4}M$ cimetidine under the same conditions). Cells were also stimulated with 8 bromo cAMP and inhibition of stimulated uptake was assayed in the presence of whole *H. pylori* or sonicated organisms, *C. jejuni* or cimetidine $10^{-4}, -5, -6M$. In contrast, the use of bacterial supernatants (media) had no effect on inhibiting stimulated acid secretion, suggesting that the inhibitor was present in very low concentration. This hypothesis was confirmed by concentrating the bacterial supernatants over an Amicon filter and re-assaying the concentrate. The inhibition of uptake of $[^{14}C]AP$ by concentrated supernatants was comparable to that exhibited by the whole organism or by the sonicate. In the case of cells stimulated by 8 bromo cAMP, $10^{-4}M$ cimetidine did not inhibit stimulation of the cells. However, *H. pylori* sonicates inhibited the stimulation by 89%. This data suggests that the target in the parietal cells is the post receptor complex, beyond the action of cAMP, possibly at the level of $H^+/K^+$ ATPase and may be an inhibitor of the enzyme or may cause alteration of calcium metabolism.

The finding of profound acid inhibition by a bacterium is unexpected, and could possibly be due to non-specific bacterial inhibition by an ubiquitous substance, such as bacterial lipopolysaccharide. However, this has been shown not to be the case because use of *C. jejuni* in the assay system demonstrated that this organism had a negligible effect on inhibiting acid secretion. *C. jejuni* is comparable in morphology to *H. pylori*, contains antigens cross-reactive with *H. pylori* antigens and is an intestinal pathogen. Perez-Perez, G. I. and M. J. Blaser, *Infect. Immun.*, 55:1256–1263 (1987). The fact that this organism had no significant inhibitory capability makes it unlikely that such bacterial products are the inhibitory factor.

Preliminary characterization of the sonicates of the *C. pylori* has been done. Heating the bacterial sonicates suggests that the inhibitory factor is moderately heat stable. That is, the inhibitory factor is partially inactivated when kept at 60° C. for 30 minutes, but completely inhibited by boiling for 30 minutes. Degradation with trypsin, even over a prolonged incubation period, had no effect on the inhibitor. However, degradation with pronase, a less specific protease, resulted in destruction of the activity of the inhibitor, suggesting that the inhibitor is at least in part comprised of protein and that inactivation of the protein component is required for total loss of inhibitor activity. Preliminary sizing of the inhibitor, using dialysis, showed that the inhibitor is larger than the molecular weight cutoff of the dialysis tubing used (i.e., approximately 12–14,000 kD). The concentration of the inhibitor has been shown to be low; dilution of the sonicate to 1:5 partially reduces the activity, and dilution to 1:10 results in loss of the effect. This is consistent with the concentration needed to see an effect with bacterial supernatants.

As a result, a new substance, which can be used as an agent or a drug to reduce (decrease or eliminate) acid secretion by parietal cells, is available. The substance has been shown to be proteinaceous in nature (i.e., a protein or, at least, a protein containing), to be moderately heat stable, to be unaffected by treatment with trypsin and to be inactivated by treatment with pronase. Thus, for the first time, a substance of bacterial origin capable of inhibiting parietal cell acid secretion has been identified and isolated As used herein, the term isolated acid inhibitor of bacterial origin is intended to include an acid inhibitor from a bacterial species, particularly Helicobacter species, such as *H. pylori* (previously known as *C. pylori*), *H. felis* and a Helicobacter-like organism isolated from Rhesus monkey, as well as other proteins which have amino acid sequences similar to that of a Helicobacter acid inhibitor. Such an acid inhibitor can be removed or isolated from a bacterium or synthesized, using known techniques such as genetic engineering and mechanical or chemical methods, to have the same or a similar amino acid sequence and/or acid inhibitory function as that of an inhibitor obtained from the bacterium. For purposes of the present invention, an amino acid sequence is similar to that of the Helicobacter product if the resulting peptide or protein exhibits an acid-inhibiting function like that of the Helicobacter product, as demonstrated by uptake and retention of $[^{14}C]AP$ within parietal cells using the previously-described assay.

The isolated substance, referred to herein as an acid inhibitor of bacterial origin, can now be produced, using known techniques (e.g., column chromatography), in quantities sufficient for sequencing and additional characterization. Using the same technique as described herein for identification of the acid inhibitor from *C. pylori*, similar substances can be identified in other bacteria (e.g., other gastric *Spirilla, E. coli*).

Sequencing and further characterization of the acid inhibitor can be carried out using known techniques. Once the acid inhibitor has been sequenced, it can be synthesized mechanically or chemically. Further characterization of activity of less than the entire *H. pylori* protein (of *H. pylori* peptides) will demonstrate whether all of the protein or only a selected portion or selected portions is/are necessary for the inhibitory effect. Analogues of the acid inhibitor or modified acid inhibitors (e.g., those in which one or more amino acids are altered/differ from the amino acid sequence of the naturally-occurring protein) can also be used.

The acid inhibitor can be administered orally or parenterally (e.g., intravenously) for the purpose of reducing acid production in an individual and, thus, for the purpose of treating peptic ulcers and other gastroduodenal conditions. As used herein, the term reducing acid production means decreasing production to a level below that (including 0 or total inhibition) at which acid would be produced in the absence of the inhibitor. The form in which the acid inhibitor is administered varies depending on the route of administration. If administered orally, the acid inhibitor will generally be included in a therapeutic composition which may also include an appropriate carrier, a flavoring agent and a sweetener. If administered parenterally, it will generally be a component of the therapeutic composition which can also include, for example, a physiologically appropriate carrier, such as physiological saline. The quantity of the acid inhibitor to be administered to an individual will depend on many factors, such as the size of the individual and the severity of the individual's gastric or duodenal conditions. Generally, the acid inhibitor of the present invention will be administered once to several times each day, depending on the method of administration (e.g., at times at which acid production would normally be increased). *H. pylori* is resident in the stomachs of many, if not most, individuals with peptic ulcers and has been shown to be "on" (produced initially in such individuals and subsequently to be turned "off"). Thus, it is also possible, using genetic engineering techniques, to alter the usual pattern and turn expression of the protein back on (or prevent it from being turned off) and provide a method of in vivo or endogenous manipulation of *H. pylori* which is a therapeutic method. The acid inhibitor of *H. pylori* origin is useful in reducing acid secretion, such as in an individual whose parietal cells overproduce acid or in an individual with peptic ulcers. In addition, it is useful in identifying similar acid inhibitors produced by other organisms. For example, antibodies specific for (reactive with or able to bind to) the *H. pylori* acid inhibitor can be produced and used to identify products from other organisms which are cross-reactive with the *H. pylori* acid inhibitor. Alternatively, an oligonucleotide whose sequence encodes a portion of the acid inhibitor of *H. pylori* can be produced and used to probe a library of DNA from another bacterium for sequences which hybridize with it. The sequences so obtained can be expressed in an appropriate host and isolated and the encoded product tested, as described herein, for acid inhibiting activity.

The present invention will now be illustrated by the following Examples, which are not to be seen as limiting in any way.

EXAMPLE 1

Demonstration of the Ability of the *H pylori* Product to Reduce Acid Secretion

Bacterial culture: Three isolates of *H. pylori (C. pylori)* were obtained from each of three patients with duodenal ulcer, erosive gastritis and histologically normal gastric mucosa, respectively. Each isolate conformed to standard phenotypic criteria for *H. pylori* and were grown on biphasic media under microaerophilic conditions at 37° C. for 72 hours. Bacteria were used at an $OD_{600}$ of approximately 1.0, equivalent to approximately $1.5 \times 10^8$ cfu.

Gastric epithelial cells: Male New Zealand rabbits, weighing 5-6 pounds were killed by intravenous pentobarbital sodium (nembutal) overdose. The gastric fundus and body were removed and the mucosa was removed. Epithelial cells were isolated by a modification of the method of Soll. Soll, A. H., *J. Physiol.*, 238:366-367 (1980). Mucosal fragments were washed twice with Hank's salt solution with 0.1% bovine serum albumin (Sigma fraction V). They were then incubed in 30 mls of basal medium Eagles (BME:Gibco) containing 0.35 mg/ml crude collagenase (Sigma) and 1 mM glutamine with pH adjusted to 7.4 and gassed with 95% $O_2$ 5% $CO_2$ at 37° C. for 15 minutes. The mucosal fragments were washed in Earle's balanced salt solution (Gibco) without $Ca++$ or $Mg++$, but with 1 mM glutamine, 10 mM Hepes and 2 mM EDTA, and then incubated at 37° C. for 10 minutes in the same solution. Three sequential incubations of thirty minutes in 50 mls of BME collagenase solution followed. After each incubation the medium containing the cell and gland suspension was centrifuged at 1000 rpm for 2 minutes and collagenase was removed with Hank's salt solution with 1% BSA. The washed cells were pooled and incubated for 5 minutes in Hank's solution containing 1% BSA and 0.2 mM dithiothreitol (DTT) (Sigma), to disrupt remaining gastric glands to yield individual cells and small glands. The DTT was removed by two washes with EBSS, 1% BSA, 1 mM glutamine and Hepes solution. [$^{14}$C]-aminopyrine accumulation: [$^{14}$C]-aminopyrine ([$^{14}$C]AP) uptake by parietal cells was used as an index of hydrochloric acid sequestration within the parietal cells. This assay is widely used as an indirect measure of $H^+$ ion secretion by parietal cells because the loss of polarity that occurs with isolated cells prevents direct measurement. [$^{14}$C]AP is a weak base that diffuses into parietal cells. Once inside, it is in a compartment with a pH below its pKa of 5.0 and is thereby converted into a largely ionized form, which is poorly diffuseable across membranes. Thus, the accumulation of [$^{14}$C]AP reflects acid production by the parietal cell. This technique was used to demonstrate alterations in stimulated acid production in the presence of *H. pylori*, and then as an assay for the inhibitory factor associated with the organism.

Equal volumes of epithelial cell suspension ($1 \times 10^6$ cells/ml) in EBSS medium were incubated at 37° C., after gassing with $O_2/CO_2$, and contained dinitrophenol (DNP) $10^4 M$, PBS buffer or the material under test. After 2 hours, 0.2 lCi/ml of [$^{14}$C]AP (New England Nuclear) was added to each suspension, and incubated for a further 5 minutes at 37° C.

Histamine diphosphate (Sigma) $10^{-4} M$ and isobutylmethyl xanthine (IMX:Sigma) $10^{-5} M$ were added to stimulate the parietal cells to accumulate [$^{14}$C]AP. Cimetidine $10^{-4} M$ to $10^{-6} M$ was used as a positive control, as it is a known inhibitor of the accumulation of [$^{14}$C]AP. No addition of histamine and IMX was made to the basal or DNP aliquot. The DNP treated cells provided a measure of [$^{14}$C]AP that bound nonspecifically. After 20 minutes of incubation, triplicate aliquots of 500 11 were removed from each reaction tube and were added to tubes containing 1 ml of EBSS solution and centrifuged for 30 seconds. The [$^{14}$C]AP in the pellet was counted by liquid scintillation and expressed as cpm/$10^6$ cells. The aminopyrine uptake was calculated as:-[$^{14}$C]AP uptake of test samples - [$^{14}$C]AP uptake of DNP cells [$^{14}$C]AP basal uptake - [$^{14}$C]AP uptake by DNP treated cells.

Assessment of epithelial cell viability: Possible toxic effects of *H. pylori* on gastric epithelial cells were assessed by protein synthesis, as measured by $^3$H-leucine incorporation. Tritiated leucine (6 lCi/ml) was added to aliquots of cells under the conditions above. At 60 minutes, triplicate samples were removed, cells were pelleted, and percipitable counts were measured by liquid scintilaton counting.

Protease treatment: Pronase 1 (Calbiochem) was used to digest the sonicates for 30 minutes at 37° C. at 50 lg/ml. Trypsin was used overnight at 37° C. at 0.25%.

Bacterial Growth: The three isolates of *H. pylori* all grew well on serial culture in biphasic media and were used 48-72 hours after the initiation of the culture. Culture of two randomly selected preparations of rabbit gastric mucosa did not reveal any evidence of *H. pylori*-like organisms.

Figure 1:
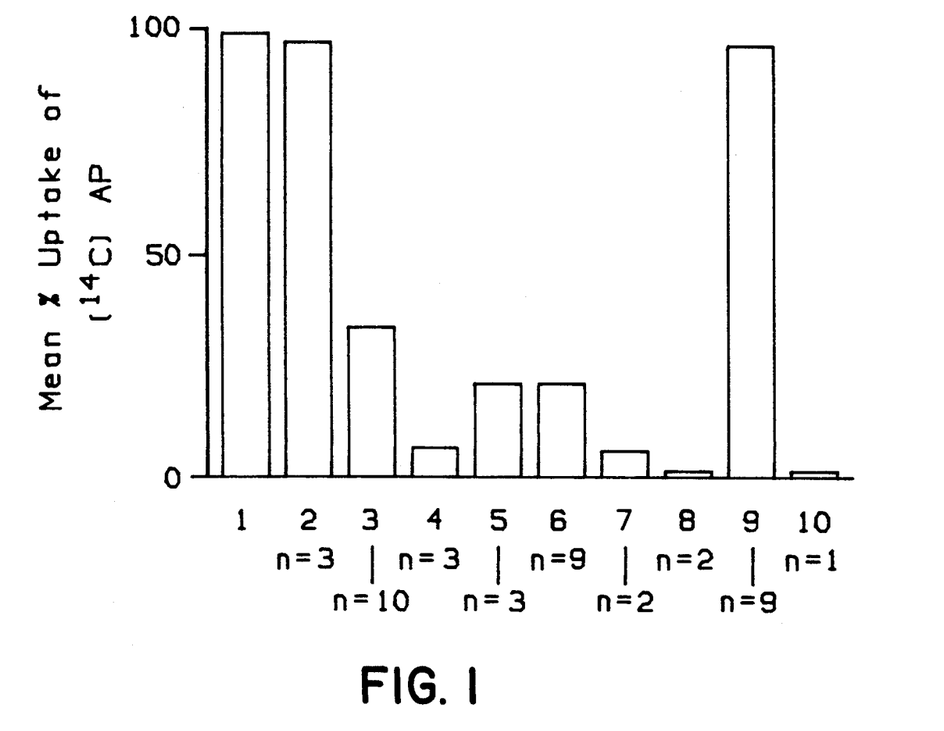
FIG. 1 is a graphic representation of differences in stimulated [$^{14}$C]-amino pyrine uptake by rabbit gastric epithelial cells under a variety of conditions: 1=histamine and IMX stimulated cells; 2=stimulated plus C.jejuni; 3,4,5=inhibition by isolate 1, 2 and 3, whole organisms; 6,7,8=inhibition by isolate 1, 2 and 3, sonicates; 9=isolate 1 supernatant; 10=isolate 1 supernatant, concentrated 10:1.

The absolute values of the stimulated uptake of [$^{14}$C]aminopyrine varied form individual experiment to experiment. The data for each experiment was therefore normalized by expressing the uptake of the [$^{14}$C]AP as a percentage of the stimulated value which was taken to be 100%. As represented in FIG. 1, the addition of a different strain of Campylobacter (*C. jejuni*) to the stimulated cells had no significant effect on [$^{14}$C]AP uptake. The addition of the three isolates of *H. pylori*, either as the whole organism or as the sonicate, reduced the stimulated uptake of [$^{14}$C]AP by 65.8–100%. The supernatant of isolate 1 was investigated in 9 experiments and did not reduce the uptake of [$^{14}$C]AP. However, when that supernatant was concentrated 10 fold on an Amicon PM10 filter, the effect seen with the sonicate was reproduced.

Figure 2:
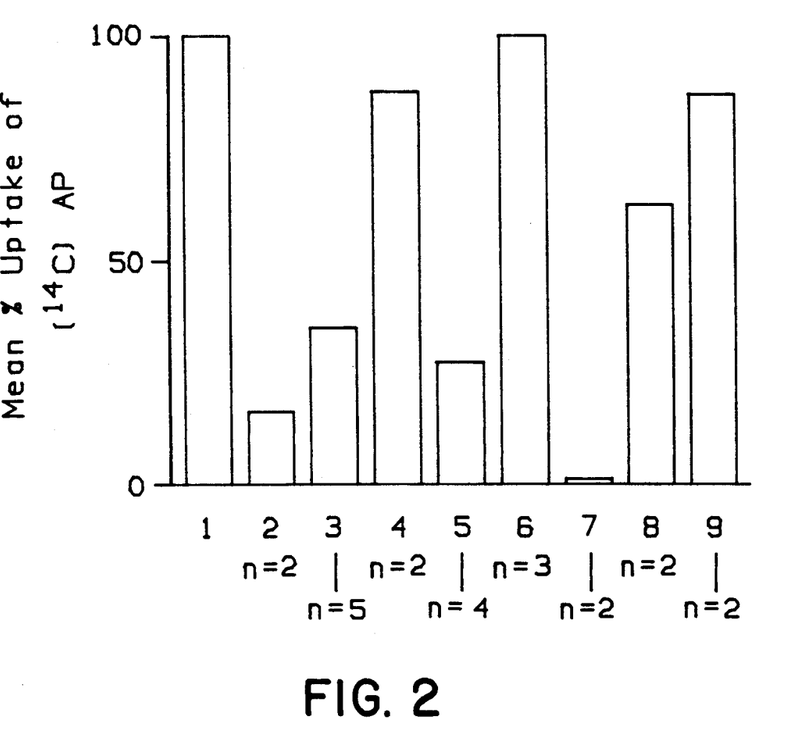
FIG. 2 is a graphic representation of differences in stimulated [$^{14}$C]-aminopyrine uptake by rabbit gastric epithelial cells under a variety of conditions: 1=Histamine and IMX stimulated cells; 2=Cimetidine $10^{-4}$M; 3=Sonicate treated at 60° C. for 30 minutes; 4=Sonicate treated at 100° C. for 30 minutes; 5=Sonicate treated with trypsin 0.25%; 6=Sonicate treated with pronase; 7=Sonicate dialyzed; 8,9=Sonicate diluted 1:5, 1:10.

To confirm that the inhibition demonstrated was comparable to that of known acid inhibitors, cimetidine was used at $10^{-4}$M and gave inhibition of 83.1% (FIG. 2). The effect of cimetidine at $10^{-5}$ and $10^{-6}$M was assessed; 5.6% and 0% reduction of uptake occurred, respectively.

EXAMPLE 2

Determination of Characteristics of the *C. pylori* Product

Physical properties of sonicates of the *H. pylori* isolate were assessed; results of that assessment are represented graphically in FIG. 2. Heat treatment of the sonicate at 60° C. for 30 minutes produced no significant diminution of the effect of the untreated sonicate. However, heat treatment of the sonicate at 100° C. for 30 minutes almost entirely eliminated any inhibitory effect on stimulated uptake of [$^{14}$C]AP. Inactivation studies with trypsin and pronase revealed discordant results. The inhibitory effect of the sonicate was eliminated by pronase treatment, but trypsin treatment had little or no effect. Furthermore, dialysis of the sonicate did not eliminate the inhibitory effect, whereas sequential dilution of sonicate gave progressive diminution of the inhibitory effect. The inhibition of the stimulated uptake of $^{14}$CAP could obviously be the result of cytotoxicity. This possibility was examined by measuring the cells' capacity to synthesize protein. The data in the Table make it apparent that there was not significant reduction of the incorporated tritiated leucine in conjunction with *H. pylori*.

TABLE $^{3}$H-Leucine Incorporation into Gastric Epithelial Cells After 1 Hour

| ADDITIONS TO CELLS | | CPM + (SD) |
|---|---|---|
| A. | BASAL | 140,458 + 6898 |
| B. | HISTAMINE + IMX | 141,447 + 3644 |
| C. | DINITROPHENOL | 3228 + 86 |
| D. | C. PYLORI | 138,461 + 3872 |
| E. | C. PYLORI + HIST + IMX | 141,478 + 4591 |

A,B,D,E p > 0.05 between each.

EXAMPLE 3

Demonstration of the Ability of Helicobacter from other Species to Reduce Acid Secretion

Bacterial Cultures

The following strains of bacteria were used in the parietal cell assays: three subcultures of *H. felis* (ATCC strain); a clinical strain of *H. pylori* (Hpwin); *H. mustelae* strains Cm4720, 4726 and an isolate from a Rhesus monkey, kindly provided by Dr. Andre DuBois, Walter Reed Army Hospital, Bethesda, Md. An isolate of *C. jejuni* (T18), clinical strains of *E. coli*, *P. vulgaris*, and *K. oxytoca*.

Bacterial Cell Suspensions

*H. pylori*, *H. mustelae*, *H. felis*, a Helicobacter like isolate from a Rhesus monkey and *C. jejuni* were grown on campylobacter selective agar plates (Skirrow's media) for 2 to 3 days at 37° C. and subsequently on blood agar alone in a microaerophilic environment.

*E. coli*, *P. vulgaris* and *K. oxytoca* were grown on sheep blood agar for 24 hours at 37° C. Cells were harvested in sterile physiological saline using cotton wool swabs and washed twice in saline.

The concentration of the organisms was adjusted to an $OD_{600}$ reading of 1.00 in saline.

In thermal experiments aliquots of the above suspensions were heated to 60° C. for 30 minutes in a shaking water bath. For sonicates, similar suspensions were sonicated on ice at a setting of 7 using a microtip (Heat System-Ultrasonics Cell Disruptor W-220F Plainview, N.Y. 11803) in 4, 30 sec consecutive treatments.

In Vitro Assay of Parietal Cell Activity: $^{14}$C-Aminopyrine Accumulation

The method as previously described was used (Cave, D. R. and M. Vargas, Lancet, 2:187–189 (1989)). In brief, a rabbit stomach was washed and the body and fundus were cut up into small pieces in Hank's tissue culture fluid, and then treated with collagenase at 37° C. Three successive 30 minute treatments provided an excellent yield of small glands and single epithelial cells. Aliquots of these cells (approximately $1 \times 10^6$ per/ml) were gently shaken with the test suspensions in a shaking water bath at 37° C. for 2 hours. At the end of this period $^{14}$C-aminopyrine, histamine and the phosphodiesterase inhibitor, isobutyl methylxanthine (IMX) were added. Appropriate controls with no histamine or IMX 9 basal) and DNP to kill the cells (nonspecific binding) were included. After incubation, triplicate samples were centrifuged in 1.5 ml microfuge tubes. The tips were cut off and cell pellets digested with sodium hydroxide. After neutralization, aqueous scintillation cocktail was added and samples were counted. An accumulation ratio of $^{14}$C-AP accumulated in stimulated parietal cells relative to that in treated cells, minus basal uptake medium after subtraction of the radioactivity non-specifically bound to the DNP killed cells, was calculated. To compare the effect of each bacterial preparation, results are expressed as a percentage inhibition of $^{14}$C accumulation in those cells incubated with a bacterial suspension compared to stimulated parietal cells. Data were normalized to percentages because day to day variations of ratios with cells obtained from different animals made direct comparison impractical.

Figure 3:
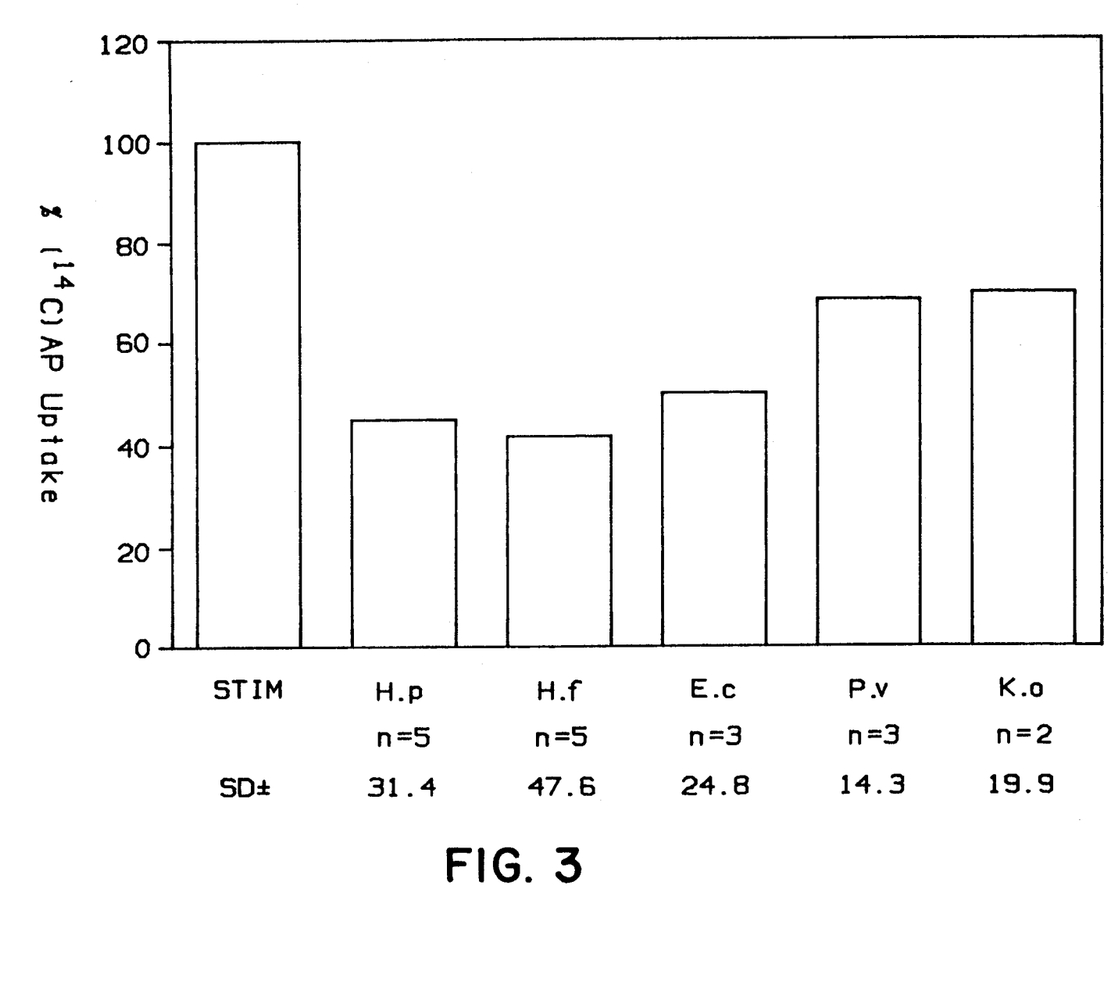
FIG. 3 is a graphic representation of the effect of prior heating of bacteria to 60° C. for 30 minutes on uptake of $^{14}$C-aminopyrine by rabbit parietal cells. Hp=*H. pylori*. Hf=*H. felis*. Ec=*E. coli*. Pv=*P. vulgaris*. Ko=*K. oxytoca*.
Figure 4:
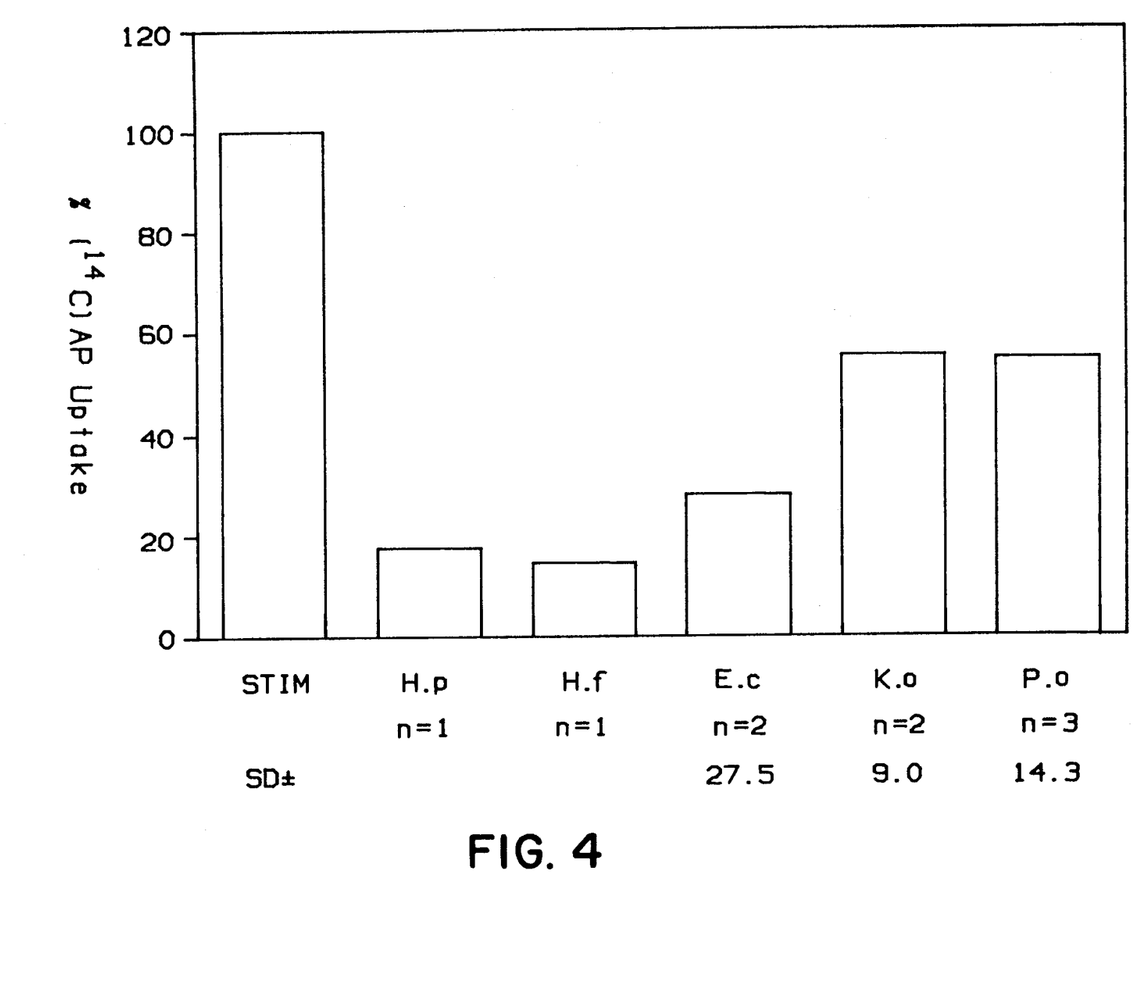
FIG. 4 is a graphic representation of the effect of cell free sonicates of bacteria on the uptake of 14$_C$-aminopyrine by rabbit parietal cells: Stim=stimulated. Hp=*H. pylori*. Hf=*H. felis*. Ec=*E. coli*. Pv=*P. vulgaris*. Ko=*K. oxytoca*.
Figure 5:
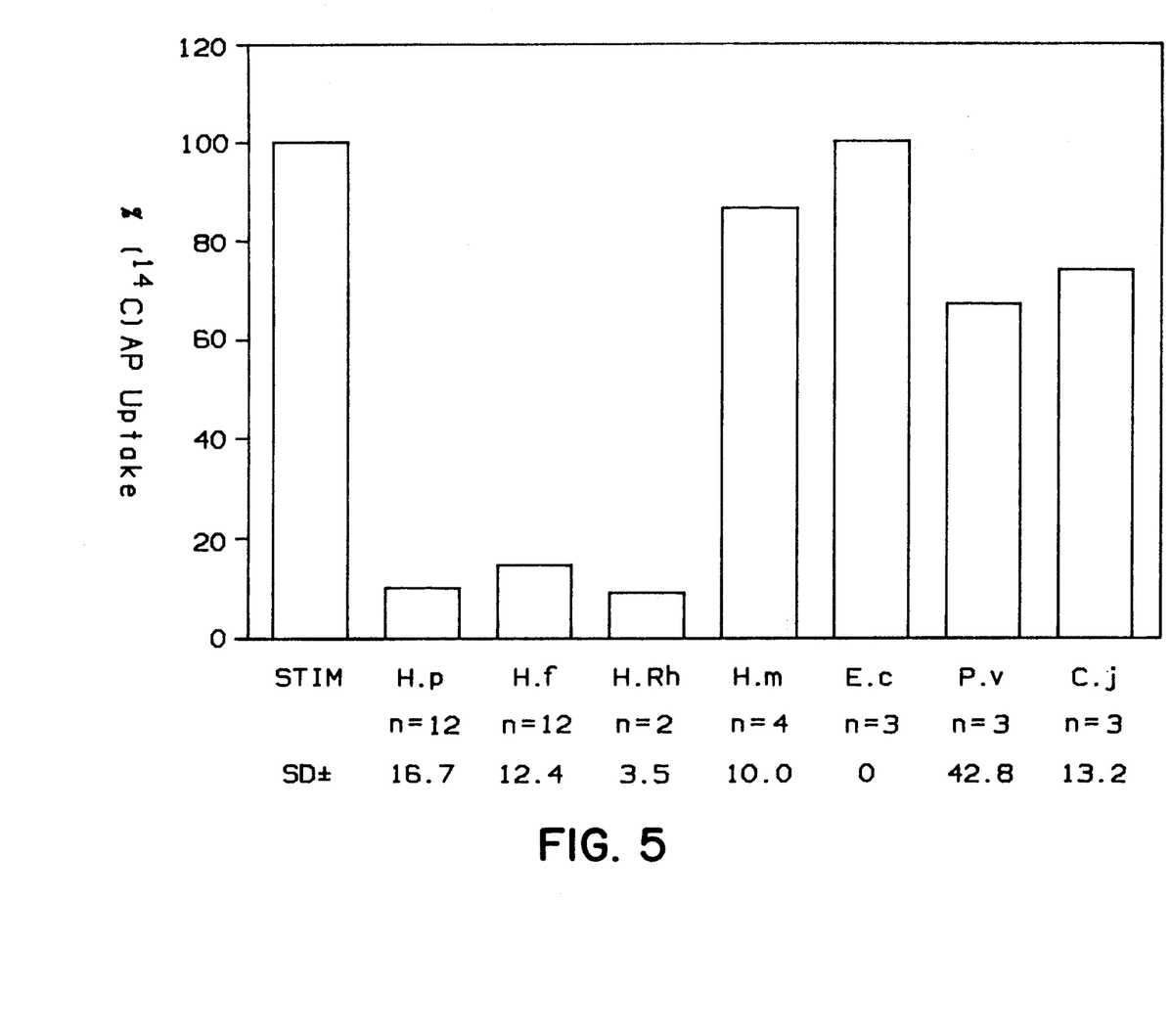
FIG. 5 is a graphic representation of the effect of whole bacteria on the uptake of $^{14}$C-aminopyrine by rabbit parietal cells: Stim=stimulated, Hp=*H. pylori*, Hf=*H. felis*, H.Rh=isolate from Rhesus monkey, H.m=*M. mudelae* Ec=*E. coli* PV=*P. vulgaris*, Cj=*C. jejuni*.

Results of these assays showed that *H. pylori* inhibited the accumulation of $^{14}$C-AP uptake by parietal cells (FIG. 3) and that *H. felis* and an isolate from a Rhesus monkey proved to be equally inhibitory to $^{14}$C-AP accumulation as their human counterpart. By contrast, 3 strains of *H. mustelae* (pooled results) had little effect on the accumulation of $^{14}$C-AP. Two urease producing control bacteria, *P. vulgaris* and *K. oxytoca*, and one other facultative anaerobe, *E. coli*, along with *C. jejuni* reduced $^{14}$C-AP accumulation by less than 35%. It is likely that there was some variation in bacterial numbers of these control organisms because an OD$_{600}$ of 1 was used for standardizing comparisons, rather than absolute counts of colony forming units. Furthermore, some bacterial growth may have occurred during the 2 hour incubation period, when whole bacteria were under study. The use of bacterial sonicates instead of whole bacteria (FIG. 4) had little influence on $^{14}$C-AP accumulation, as far as *H. pylori* and *H. felis* were concerned. However, *E. coli* and both *P. vulgaris* and *K. oxytoca* sonicates reduced $^{14}$C-AP accumulation to lower levels than the intact organism, suggesting release of products that interfered with the assay. Whole bacteria were heated to 60° C. for 30 minutes (FIG. 5). This revealed some heat lability for *H. pylori*, increasing uptake of $^{14}$C-AP to 42% and for *H. felis* to 41.6%. A modest further inhibition occurred with heating the whole control organisms, giving results comparable to the sonicated bacteria.

Equivalents

Those skilled in the art will recognize, or be able to ascertain using no more than routine experimentation, many equivalents to the specific embodiments of the invention described herein. Such equivalents are intended to be encompassed by the following claims.

I claim:

1. A method of inhibiting production of acid by mammalian gastric parietal cells, comprising contacting the parietal cells with a proteinaceous acid inhibitor substance obtained by sonicating Helicobacter species bacteria, said substance being capable of inhibiting acid production by mammalian gastric parietal cells.

2. A method of claim 1, wherein the proteinaceous acid inhibitor substance is obtained by sonicating *Helicobacter pylori* bacteria.

3. A method of claim 2 wherein the proteinaceous acid inhibitor substance is non-dialyseable, heat-sensitive and pronase-sensitive.

* * * * *